(12) United States Patent
Wyzgala

(10) Patent No.: US 6,626,923 B1
(45) Date of Patent: Sep. 30, 2003

(54) BRAKE ACTIVATOR SYSTEM FOR A ROTATIONAL ABLATION DEVICE

(75) Inventor: Mark H. Wyzgala, Bellevue, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 371 days.

(21) Appl. No.: 09/721,348

(22) Filed: Nov. 22, 2000

(51) Int. Cl.$^7$ ................................................ A61B 17/00
(52) U.S. Cl. ........................ 606/159; 606/180; 606/170
(58) Field of Search .............................. 606/79, 80, 84, 606/159, 167, 169, 170, 171, 180; 604/164.07, 164.13, 165.04, 167.03, 167.02, 167.05

(56) References Cited

U.S. PATENT DOCUMENTS

| 3,712,386 | A | * | 1/1973 | Peters | ........................ | 606/170 |
| 5,287,858 | A | * | 2/1994 | Hammerslag et al. | ...... | 606/170 |
| 5,415,170 | A | * | 5/1995 | Hammerslag et al. | ...... | 606/170 |
| 6,149,663 | A | * | 11/2000 | Strandberg et al. | ......... | 606/180 |
| 6,503,227 | B1 | * | 1/2003 | Guo et al. | ............. | 604/164.02 |

* cited by examiner

Primary Examiner—Gloria M. Hale
(74) Attorney, Agent, or Firm—Christensen O'Connor Johnson Kindness PLLC

(57) ABSTRACT

A guide wire brake suitable for use in a rotational ablation system includes a linear actuator that when actuated, in conjunction with a brake collet, prevent a guide wire from rotating or moving axially during the rotation of the ablation burr. Multiple embodiments of the linear actuator are disclosed that use single and/or multiple bellows configurations to actuate the guide wire brake.

16 Claims, 9 Drawing Sheets

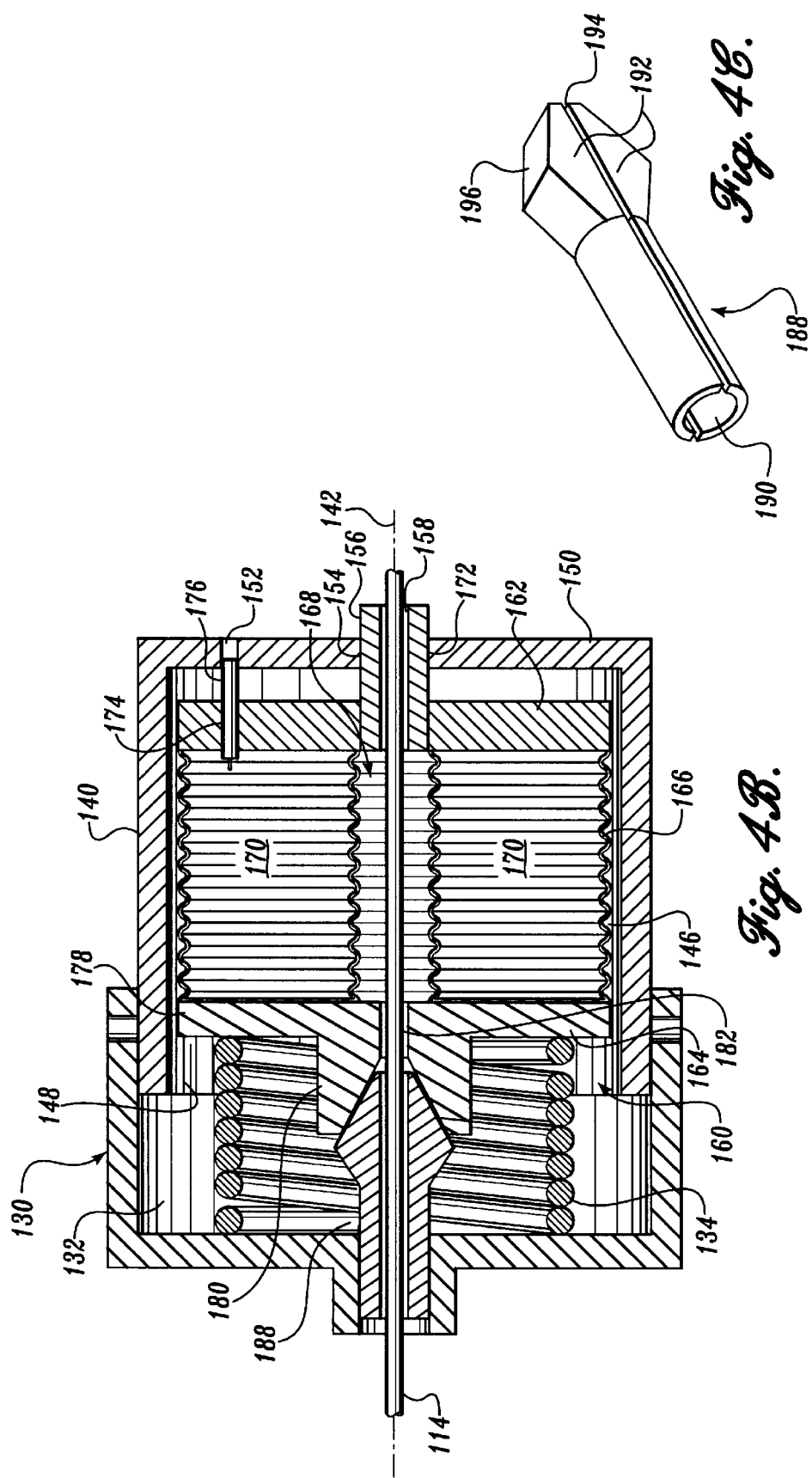

BRAKE ACTIVATOR SYSTEM FOR A ROTATIONAL ABLATION DEVICE

FIELD OF THE INVENTION

The present invention relates to atherectomy devices, in general and in particular to brake systems for use in atherectomy devices.

BACKGROUND OF THE INVENTION

Arteriosclerosis is a common vascular disease in which a patient's blood vessels become hardened and blocked by plaque or clots that impede blood flow. Left untreated, this condition is a major contributing factor to the occurrence of high blood pressure, strokes and cardiac arrest.

To treat arteriosclerosis, many invasive and non-invasive techniques have been developed. For example, cardiac bypass surgery is now a commonly performed procedure whereby an occluded cardiac artery is bypassed with a segment of a healthy blood vessel that is obtained from elsewhere in the body. While this procedure is generally successful, it is fairly traumatic because the entire chest cavity must be opened to access the occluded vessel. Therefore, the procedure is not generally performed on elderly or relatively frail patients.

One example of a minimally invasive technique that is being performed on a greater number of patients is to remove the occluding material from a patient's vessel with an atherectomy device. To perform this procedure, a guide catheter is typically inserted into the patient's femoral artery and advanced until the distal end of the guide catheter is located in the patient's ostium. A guide wire is then inserted through the guide catheter and traversed into the coronary arteries and past the occluded material to be treated. Then, as described in U.S. Pat. No. 4,990,134, issued to Auth, an atherectomy catheter having a small abrasive burr is advanced through the guide catheter and over the guide wire to the point of the occlusion. The burr is then rotated at high speed and passed through the occlusion during an ablation phase in order to remove particles that are sufficiently small such that they will not reembolize in the distal vasculature. As the burr removes the occlusion, a larger lumen is created in the vessel and blood flow is restored.

During the atherectomy procedure, after the burr has been routed over the guide wire to the location of the occlusion, the physician activates a rotational source (i.e. gas turbine) coupled to the burr by depressing a foot pedal so that the rotational source spins the ablation burr up to operational speed. In a conventional atherectomy device, a brake system is activated in unison with the rotational source to prevent rotation of the guide wire during the ablation phase of the atherectomy procedure. If the guide wire is not secured, the rotational inertia of the burr may begin to spin the guide wire and advance it downstream of the occlusion.

As shown in FIGS. 1 and 2A, a conventional brake system 20 consists of a brake cylinder 22, having a bore 24 extending therethrough. The cylinder 22 is mounted to a brake assembly bracket 26. A cylindrical piston 28 having an inner tapering or partially conical bore 30 linearly reciprocates within the bore 24 of the brake cylinder 22. A wiper ring seal 32 is seated on a front surface 34 of the piston 28 to create a chamber 38 within the bore 24. A cylindrically shaped brake collet 40 is disposed adjacent to the rear surface of the piston 28. The brake collet 40 includes an axial bore 46 for allowing the guide wire 42 to extend therethrough.

Referring to FIG. 2A–2B, the distal end of brake collet 40 further includes a pair of tapered jaws 44 that begin at approximately the mid point of the brake collet 40. The tapered jaws 44 have a conical engagement surface 50 that mates with the tapering bore 30 of the piston 28. The jaws 44 are separated by a slot 52 that extends from the distal end of the brake collet 40 toward the mid-section such that the jaws are hinged at the proximal end but can bend inward toward the exposed guide wire 42 when the jaws are forced into the tapering bore 30 of the piston 28.

The brake cylinder 22 has a gas inlet 56 that connects the chamber 38 to a source of gas through a gas conduit 58. Attached to one end of the brake cylinder 22 is a brake bracket 60. The brake bracket 60 has a centrally located bore 62 to retain the distal end of the brake collet 40 and to retain the brake collet 40 in proper alignment with the piston 28. Disposed around the brake collet 40 is a return spring 64 which exerts force on the rear face 66 of the piston 28 in order to return the piston 28 to its original location after the brake system 20 is deactivated.

With reference to FIGS. 1 and 2A, during the operation of the atherectomy device, the physician rotates the ablation burr via activation of a foot pedal. Depression of the foot pedal allows gas from a gas line 70 to enter manifold 74 having a gas conduit 58 fluidly connected to brake cylinder 22, and an outlet port 78 leading to the rotation source through tube 80. Gas entering chamber 38 through gas inlet 56 exerts pressure on the front piston face 68 thereby causing the piston 28 to linearly translate within the bore 24 of the brake cylinder 22. As the piston 28 moves linearly toward the brake bracket 60, the inner tapering bore 30 of the piston 28 engages the correspondingly conical engagement surface 50 of the brake collet 40 to urge the jaws 44 radially inward to engage with the guide wire 42. The jaws 44 of brake collet 40 clamp down onto the guide wire 42 so that the guide wire 42 is prevented from rotating. After the occlusion has been ablated, the physician releases pressure on the foot pedal to deactivate the ablation burr. When the physician releases the foot pedal, the gas is shut off from the chamber 38 allowing the biasing force of the return spring 64 to move the piston 28 linearly back toward the proximal end of the brake cylinder 22 as the gas escapes back through the gas conduit 58. This disengages the brake collet 40 from the guide wire 42. To prevent potential rotation of the guide wire, care must be taken to ensure that the driveshaft has stopped rotating before the spring 64 pushes the piston 28 towards the brake cylinder 22 thereby releasing the guide wire.

While the brake system illustrated in FIGS. 1 and 2A works well to prevent rotation of the driveshaft during the ablation procedure, the present invention seeks to improve the performance and to simplify the design by eliminating the wiper ring seal 32.

SUMMARY OF THE INVENTION

The present invention is a brake activator system comprising several linear actuators using a bellows design to decrease the leakage of gas in the brake cylinder and ensure that the guide wire is prevented from rotating during the activation and deactivation of the atherectomy device.

In one embodiment, the brake activator system comprises a housing which includes two coaxially disposed apertures for receiving a guide wire therethrough. At least one bellows is coupled to the linear actuator. A brake collet having a camming surface and a braking surface is engageable with the guide wire. Expansion of the bellows urges the braking surface of the brake collet toward the guide wire to prevent the rotation thereof.

In another embodiment, the linear actuator uses two concentrically arranged bellows to form an annular chamber. Expansion of the chamber linearly translates the rear plate of the linear actuator into engagement with a brake collet. The conical shape of each engagement surface results in the brake collet clamping down on the guide wire and thus preventing its rotation.

In yet another embodiment, the brake activator comprises a housing, a pair of bellows and a pair of brake shoes. One end of each bellows is secured to opposing interior walls of the housing. Brake shoes are attached to the other end of each bellows to form two chambers. Expansion of the chambers linearly translates the brake shoes radially inward into engagement with the guide wire to prevent its rotation.

As will be readily appreciated from the foregoing description, the present invention provides a brake activator system that eliminates the use of a sliding seal commonly used in conventional designs so that the brake activation pressure bleeds down slower, resulting in a tighter grip around the guide wire during activation of the brake. Additionally, slower bleed down provides a longer period of time for the ablation burr to stop rotating during deactivation of the brake system prior to the brake tube disengaging from the guide wire.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 4A–4C illustrate a first embodiment of the brake activator system of the present invention;

DETAILED DESCRIPTION OF THE PREFERRED EMBODIMENT

As will be explained in further detail below, the brake activator system (hereinafter referred to as "brake system") of the present invention uses a sealed bellows to linearly translate a portion of a linear actuator into engagement with a brake collet in order to urge the brake collet into a clamping engagement with a guide wire. The bellows design provides a system that has an activation source that is more replicable, thus creating a better grip on the guide wire. The bellows design should also activate at lower pressure, thus holding the guide wire better during low pressure operation. Further, because it will have less leakage, it will bleed down after use slower and will hold longer when the burr spins down at deactivation.

Figure 1:
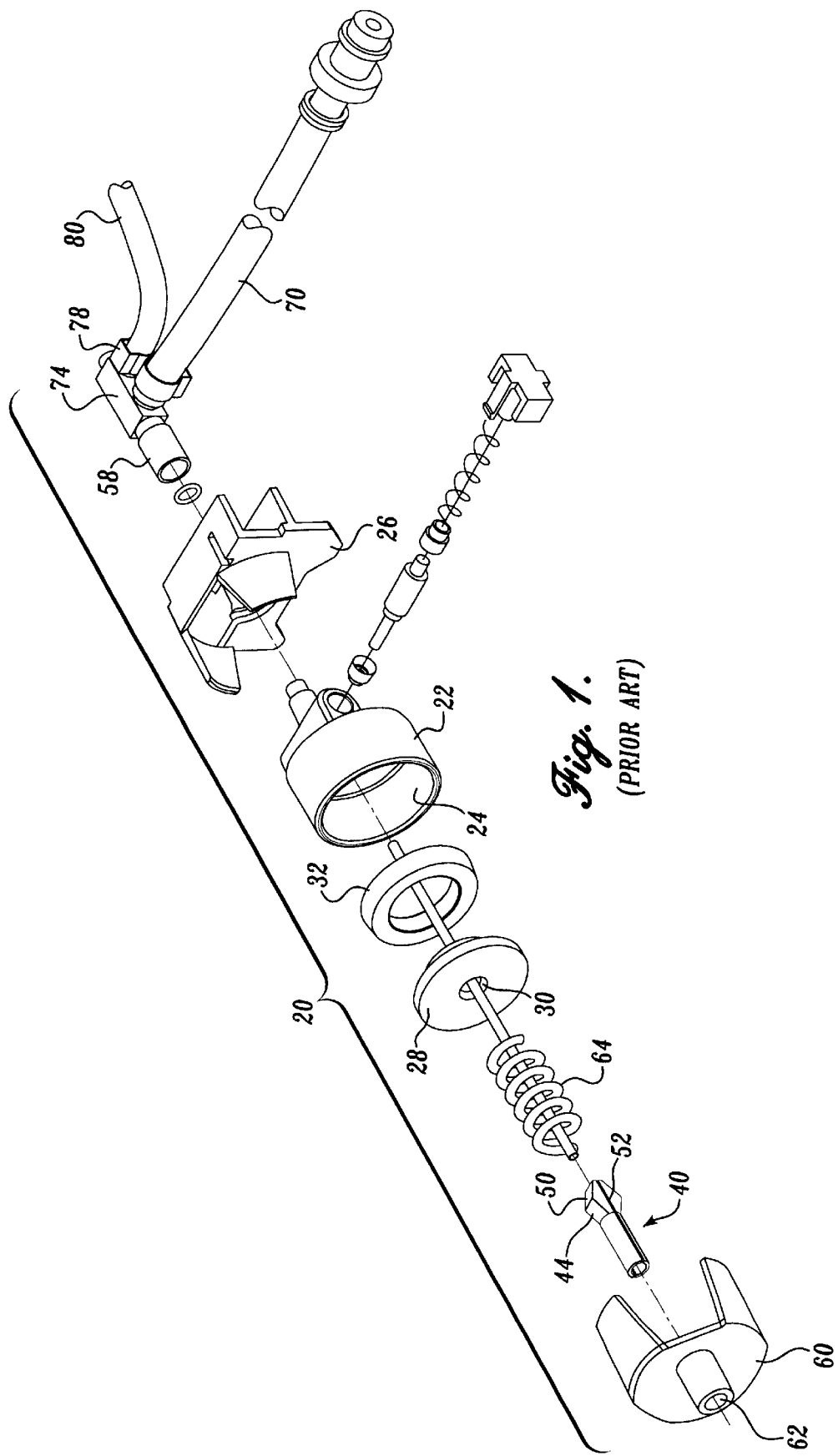
FIG. 1 illustrates an assembly view of a conventional brake system of an atherectomy burr device.
Figure 2A:
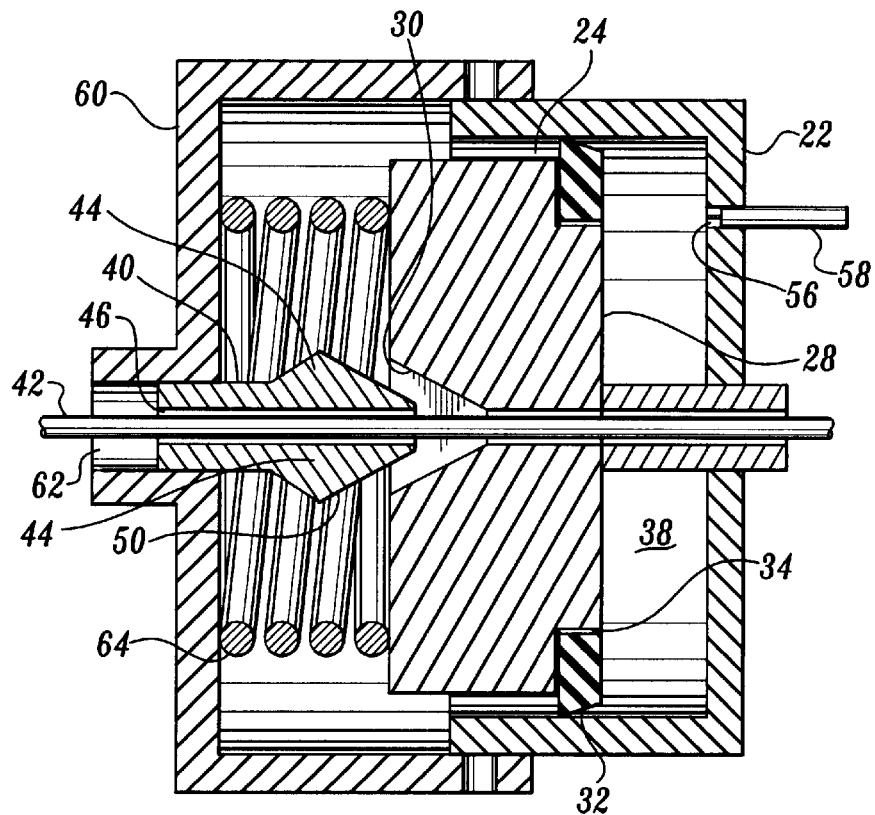
FIGS. 2A–2B illustrate the operation of a brake collet with the brake system shown in FIG. 1.
Figure 2B:
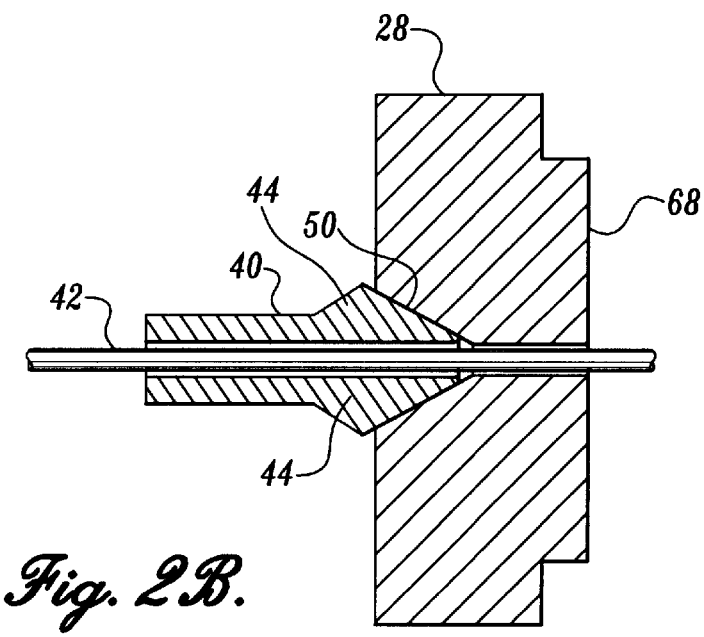
Figure 3:
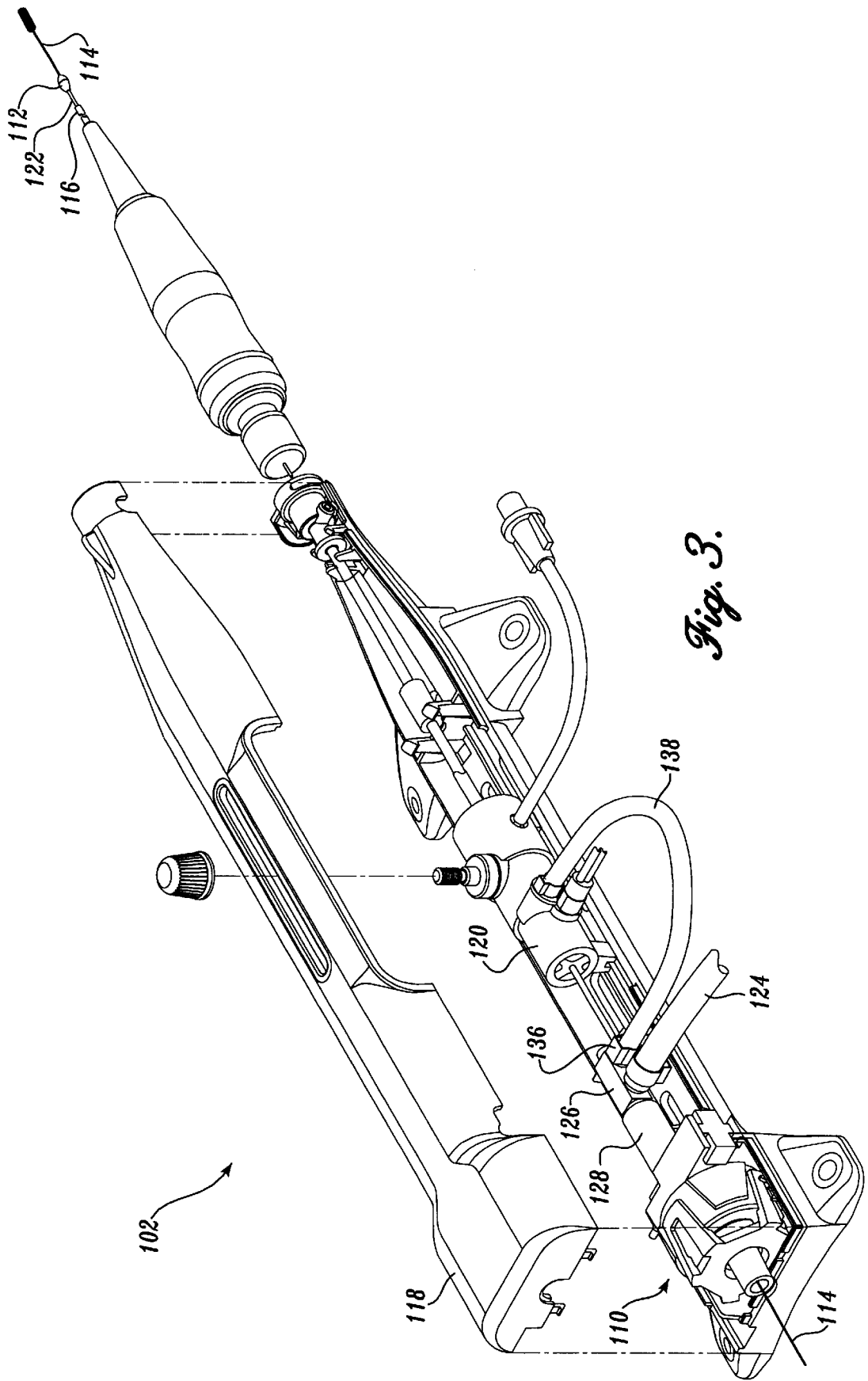
FIG. 3 illustrates an atherectomy burr device using a brake activator system of the present invention.

FIG. 3 illustrates an exemplary brake system 110 of the present invention. The brake system is utilized in conjunction with a rotational ablation burr device 102 operated by a physician in an atherectomy procedure.

A rotational ablation burr device 102 utilizes a guide wire 114 that is routed through the patient's body approximately past the location of the occlusion that is to be treated. A hollow, drive coil 122 having an ablative burr 112 at its distal end is then inserted over the guide wire 114, and advanced to a location just proximal to the occlusion. The drive coil is covered by a guide catheter 116 to minimize the impact to surrounding tissue when the drive coil 122 is rotatably engaged. The drive coil 122 is connected to a rotational source 120, such as a gas turbine, housed within an advancer housing 118.

During the atherectomy procedure, a rotational ablation burr 112 is routed over the guide wire 114 that extends from a position outside a patient's body to a position near the site of a vascular occlusion. Once the rotational ablation burr 112 is at the correct location in the patient's vasculature, the physician activates the rotational source 120 to rotate the ablation burr 112 so that a new lumen can be created. The brake system 110 is activated in unison with the rotational source 120 for preventing rotation of the guide wire 114 during the ablation phase of the atherectomy procedure and is describe in more detail below.

Figure 4A:
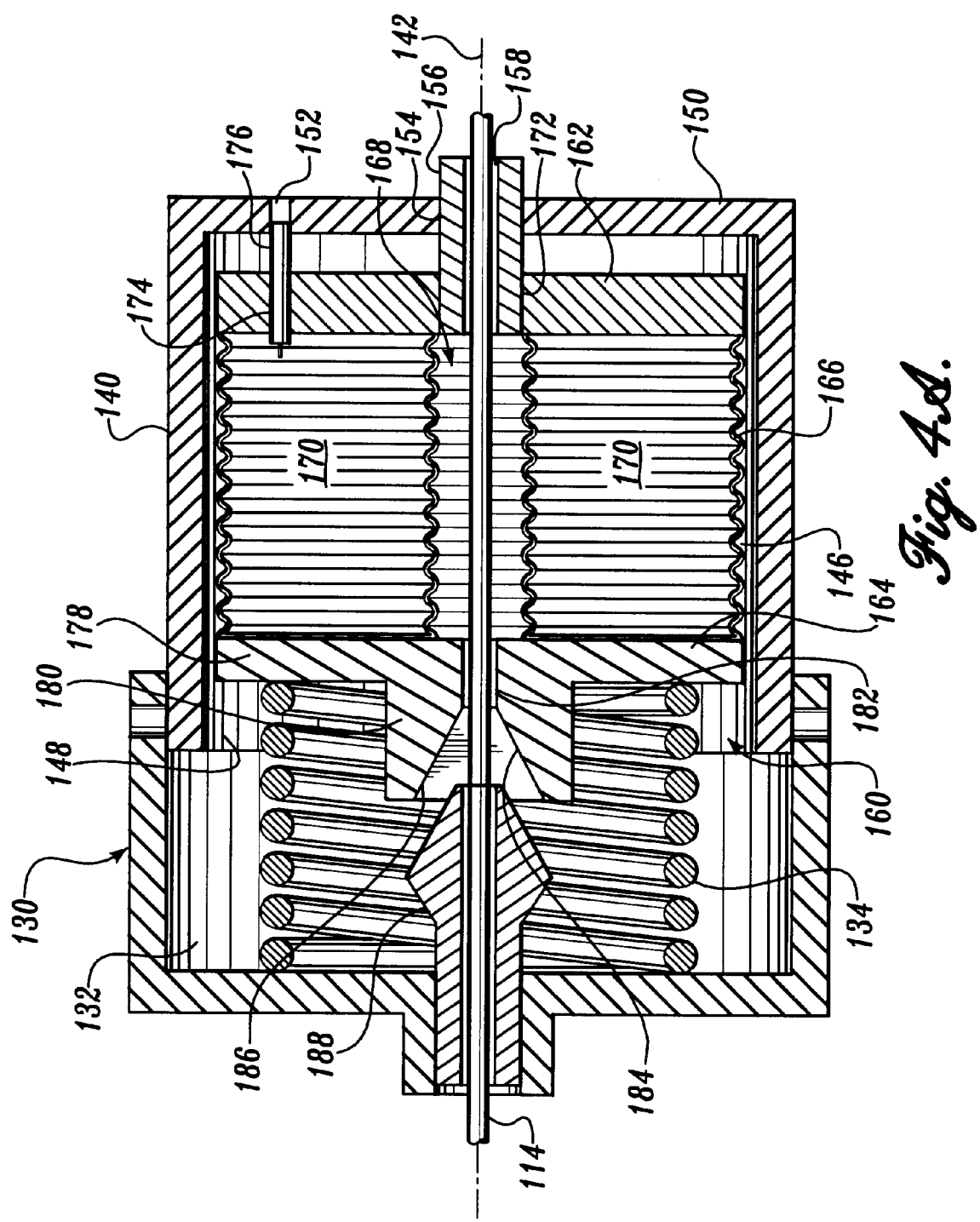

As shown in FIG. 3, the brake system 110 of the present invention is disposed at the proximal end of an advancer housing 118. As best shown in FIGS. 4A–4C, the brake system comprises a brake tube bracket 130, a brake cylinder 140, a linear actuator 160, and a brake collet 188. The brake cylinder 140 has a cylindrical bore 146 extending along its longitudinal axis 142 from the open end 148 of the brake cylinder 140 to the closed end 150 of the brake cylinder 140 and a gas inlet 152 that is in communication with a source of gas through a gas line 124 (FIG. 3). At the closed end 150 of the brake cylinder 140, and coaxial with its longitudinal axis 142 is an aperture 154. A hypotube section 156 is fitted within the aperture such that one end extends from outside the brake cylinder 140 and the other end extends within the bore 146. The hypotube section 156 has a central lumen 158 to accommodate the insertion of the guide wire 114. Coupled to the outside surface of the hypotube section 156 is front plate 162 of the linear actuator 160.

The linear actuator 160 consists of a front plate 162, a rear plate 164, and a bellows section 166. The bellows section 166 has a u-shape cross-section and extends annularly around the bore 146 of the brake cylinder 140 so that it creates an open cavity 168 that guide wire 114 extends through while providing a chamber 170 that may be expanded to apply the braking force against a brake collet 188 as described below. The open ends of the u-shape cross-sectioned bellows section 166 are bonded to the proximal surface of the front-plate 162 to create the leak-proof chamber 170.

Still referring to FIGS. 4A–4B, front plate 162 includes an aperture 172 disposed coaxially with central lumen 158 and mateable with the outer surface of the hypotube section 156. Front plate 162 is secured to the outside surface of hypotube section 156 so that one portion of the linear actuator 160 is fixed or anchored within the brake cylinder 140. Disposed radially outward of the aperture 172 is a gas inlet 174 that is in communication with the gas inlet 152 of the brake cylinder 140 via a fluid connector 176 such as a tube or pipe so that the chamber 170 receives a gas to expand the bellows section 166. Bonded to the closed end of the bellows section 166 is the rear plate 164.

As shown in FIG. 4A–4B, the rear plate 164 contains a base portion 178 and a collet engaging ring 180 that extends proximally from the center of the base portion. The base portion 178 is cylindrical in shape and has a diameter just slightly less than the inside diameter of bore 146 so that the rear plate 164 may not only reciprocate within the bore 146 but is also guided by the bore 146 so as not to get misaligned when the bellows section 166 expands. Disposed at the center of base portion 178 is an aperture 182 coaxial with the longitudinal axis 142 of the brake cylinder 140. The collet engaging ring 180 has an inner surface 184 that tapers radially inward to form a conical engagement surface 186. The diameter of the conical surface 186 at the position where the taper ends is equal to the diameter of the aperture 182 in the base portion 178.

Referring to FIGS. 4A and 4C, a cylindrically shaped brake collet 188 is disposed adjacent the proximal end of the collet engaging ring 180 of the rear plate 164. The brake collet 188 includes a bore 190 for allowing the guide wire 114 to extend therethrough. The distal end of brake collet 188 further includes a pair of tapered jaws 192 that begin at approximately the mid point of the brake collet 188. The tapered jaws 192 have a conical engagement surface 196 that mates with the conical engagement surface 186 of the collet engaging ring 180 of the rear plate 164. The jaws 192 are separated by a slot 194 that extends from the proximal end of the brake collet 188 toward the mid-section such that the jaws are hinged at the proximal end but can bend inward toward the exposed guide wire 114.

As best shown in FIG. 4A, attached to one end of the brake cylinder 140 is a brake tube bracket 130. The brake tube bracket 130 contains a bore 132 coaxial with the longitudinal axis 142 of the brake cylinder 140. The brake tube bracket retains one end of the brake collet 188 to maintain the brake collet 188 in proper alignment with the rear plate 164. Disposed around the brake collet 188 is a return spring 134 which exerts force on the proximal surface of the rear plate 164 to return the rear plate 164 to its original location after the brake system is deactivated.

With reference to FIGS. 3 and 4A–4C, during the operation of the atherectomy device, the physician rotates the ablation burr 112 via activation of a foot pedal. Depression of the foot pedal allows gas from a gas line 124 to enter manifold 126 having a gas conduit 128 fluidly connected to the chamber 170 of the bellows section 166, and an outlet port 136 leading to the rotation source through tube 138. Gas entering chamber 170 through inlets 152, 174 exerts pressure on the inside of the bellows section 166 thereby causing the rear plate 164 to linearly translate within the bore 146 of the brake cylinder 140. As the rear plate 164 moves rearward, the conical engagement surface 186 of the rear plate 164 engages the correspondingly conical engagement surfaces 196 of the brake collet 188 to urge the tapered jaws 192 of the brake collet 188 radially inward to engage with the guide wire 114.

As described above, the inside surface of the bore 146 acts as a guide so that the corresponding conical engagement surfaces are aligned properly to force the tapered jaws 192 of the brake collet 188 radially inward. The tapered jaws 192 of brake collet 188 clamp down onto the guide wire 114 so that the guide wire 114 is prevented from rotating. When the physician releases the foot pedal to deactivate the ablation burr, the gas is shut off from the chamber 170 allowing the biasing force of the return spring 134 to move the rear plate 164 linearly back toward the closed end of the brake cylinder 140 as the, gas escapes out through the gas inlets 174 and 152. This disengages the brake tube 188 from the guide wire 114.

In the presently preferred embodiment of the present invention, the bellows section 166 is made from a flexible material such as rubber, plastic, or the like, and could be fabricated by a technique such as blow-molding, which is well known in the art. Further, it will be appreciated to those skilled in the art that in an alternative embodiment, the brake cylinder 140 could be eliminated and the front plate 166 may include three or four extension or attachment members. The brake tube bracket 130 would then attach to the attachment members of the modified front plate to contain the rear plate 164 and the bellows section 166.

Figure 5A:
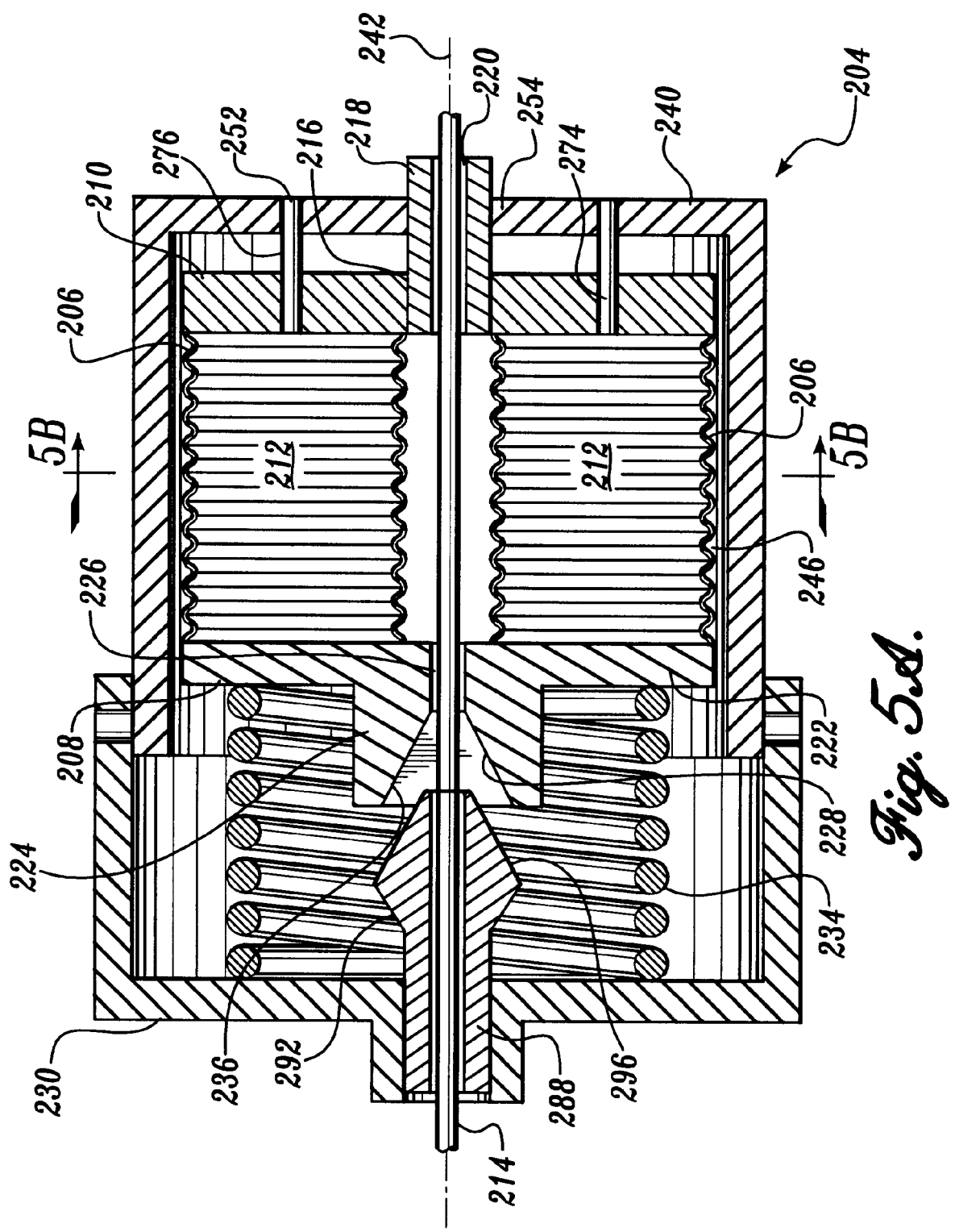
FIGS. 5A–5B illustrate a second embodiment of the brake activator system of the present invention.
Figure 5B:
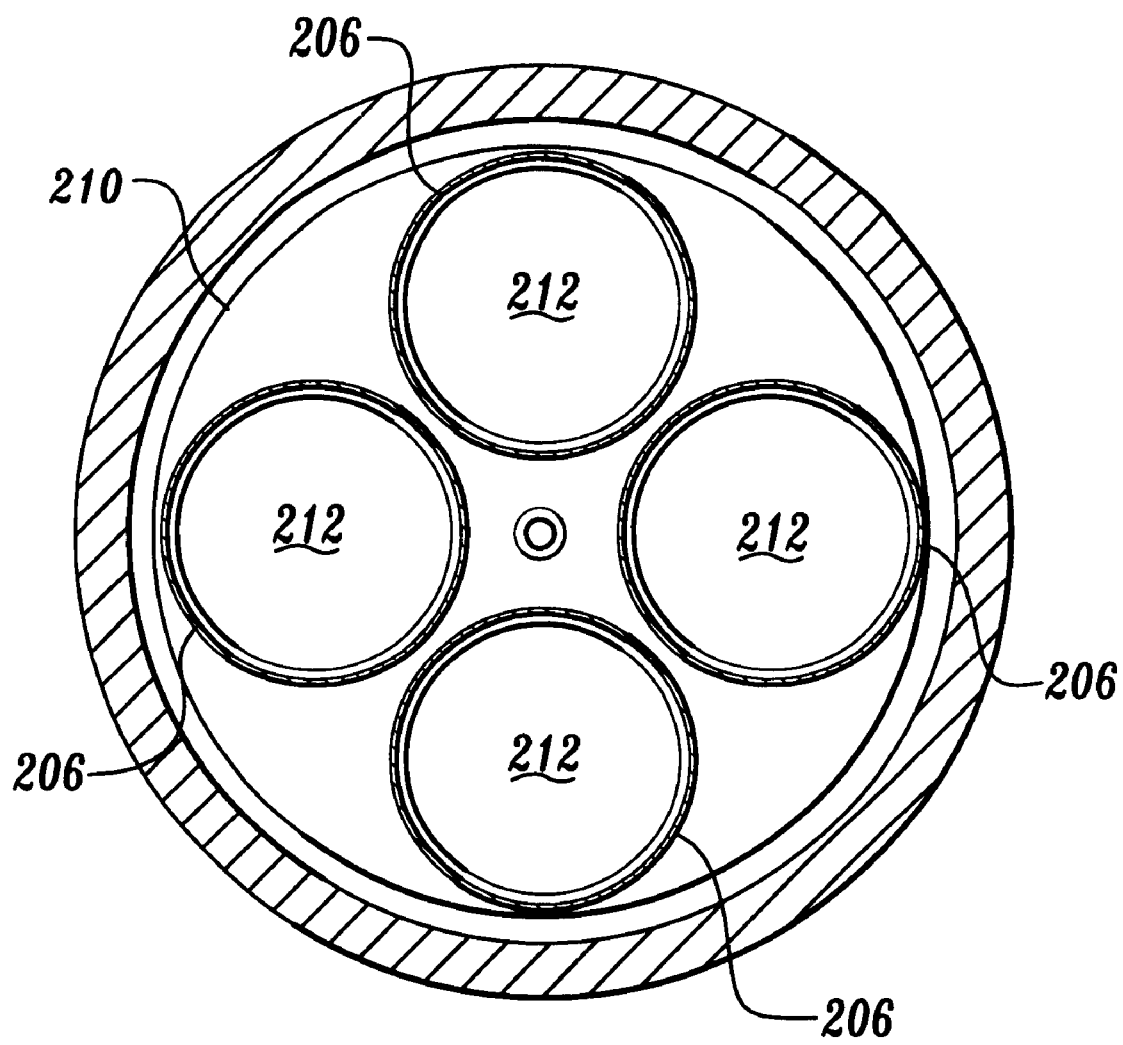

FIGS. 5A–5B illustrates another embodiment of the brake system according to the present invention. Brake system 204 contains multiple cylindrical bellows sections 206 that are disposed radially around the longitudinal axis 242 of the brake cylinder 240. The ends of the bellows sections 206 are bonded to the distal face of the rear plate 208 and the proximal face of the front plate 210, respectively, to form chambers 212. Front plate 210 includes an aperture 216 coaxial with the longitudinal axis 242 of brake cylinder 240 to receive the end of a hypotube 218. Disposed radially outward of the aperture 216 are gas inlets 274 that are in communication with gas inlets 252 of the brake cylinder 240 via a fluid connector such as a pipe or tube 276 so that the chambers 212 receive a source of gas to expand the bellows sections 206. The other end of hypotube 218 is secured to the brake cylinder 240 so that the front plate 210 is fixed or anchored. The hypotube includes a central lumen 220 for receiving a guide wire 214 therethrough.

As shown in FIG. 5A, rear plate 208 contains a base portion 222 and a collet engaging ring 224. The base portion 222 is cylindrical in shape and has a diameter just slightly less than the inside diameter of bore 246 so that the rear plate 208 may not only reciprocate within the bore 246 but is also guided by the bore 246 so as not to get misaligned when the bellows sections 206 expands. Disposed at the center of base portion 222 is an aperture 226 coaxial with the longitudinal axis 242 of the brake cylinder 240. The collet engaging ring 224 has an inner surface 228 that tapers radially inward to form a collet engagement surface 236. The diameter of the collet engagement 236 surface at the position where the taper ends is equal to the diameter of the aperture 226 in the base portion 222.

As shown in FIG. 5B, four bellows sections are used to reciprocate the rear plate 208 with respect to the stationary front plate 210. However, it will be appreciated that any number of bellows sections 206 could be used.

During operation, similar to the operation described in the first embodiment, gas is supplied to the chambers 212 of the bellows sections 206 through gas inlets 252, 274 when the physician activates the foot pedal to rotate the ablation burr. Gas entering chambers 212 exerts pressure on the front face of rear plate 208 thereby causing the rear plate 208 to linearly translate within the bore 246 of the brake cylinder 240. As the rear plate 208 moves linearly toward the brake tube bracket 230, the collet engagement ring 236 of the rear plate 208 engages the correspondingly conical engagement surfaces 296 of the brake collet 288 to urge the tapered jaws 292 radially inward to engage with the guide wire 214.

As described above, the inside surface of the bore 246 acts as a guide so that the brake collet 288 and the collet engaging ring 236 are aligned properly to force the tapered jaws 292 of the brake collet 288 radially inward. The tapered jaws 292 of brake collet 288 clamp down onto the guide wire 214 so that the guide wire 214 is prevented from rotating. When the physician releases the foot pedal to deactivate the ablation burr, the gas is shut off from the chambers 212 allowing the biasing force of the return spring 234 to move the rear plate 208 linearly back toward the distal end of the brake cylinder 240 as the gas escapes through the gas conduit 252. This disengages the brake collet 288 from the guide wire 214.

Figure 6A:
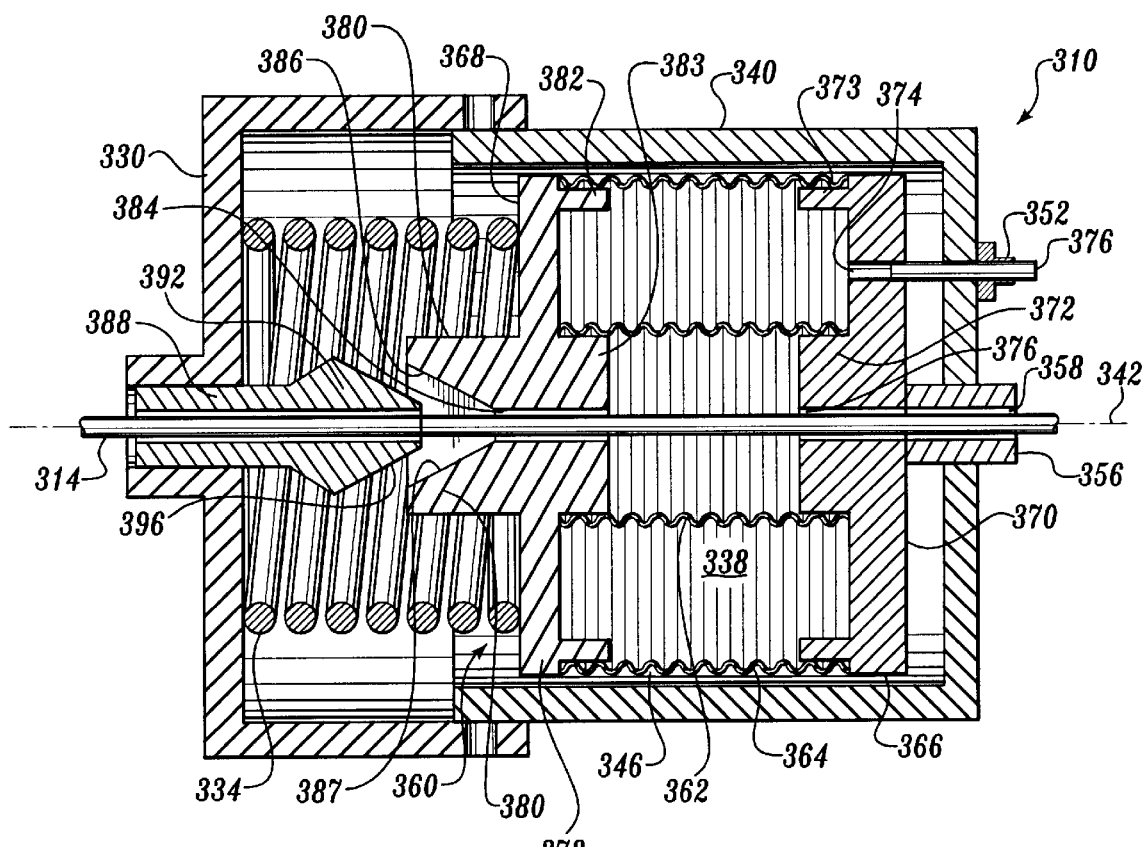
FIGS. 6A–6C illustrate a third embodiment of the brake activator system of the present invention.
Figure 6B:
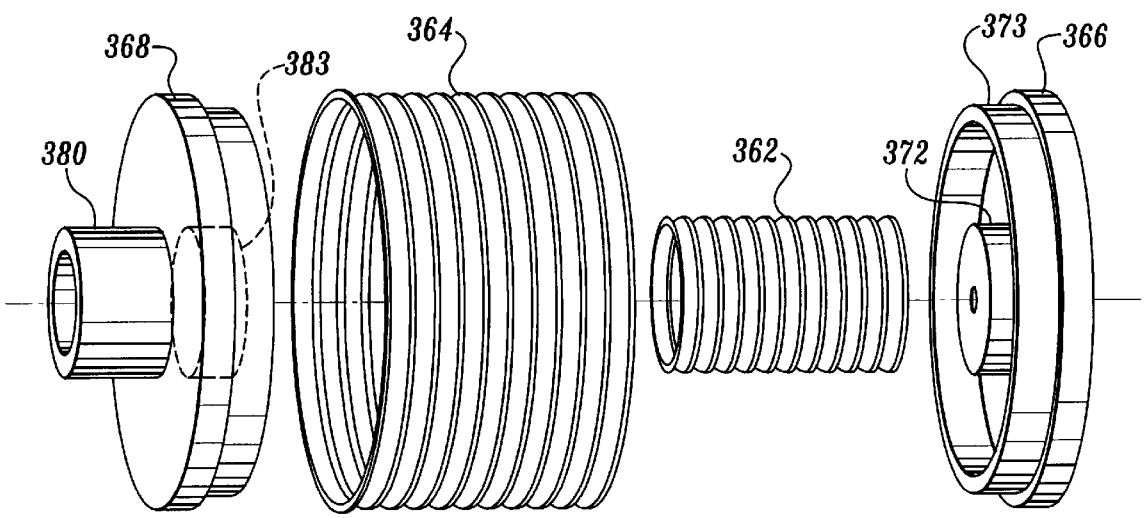

FIG. 6A–6B illustrates another embodiment of the brake system according to the present invention. The brake system 310 in this embodiment is similar to the first embodiment described above. Identical two-digit reference numerals will be used to designate similar structure found in the first embodiment but with a 300 prefix. For example, the present embodiment uses the brake cylinder 140, but will instead be numbered 340. The differences will now be enumerated below.

As shown in FIG. 6A, the brake system 310 comprises a brake cylinder 340, a brake tube bracket 330, a brake collet 388, and a linear actuator 360. The linear actuator 360 uses a different arrangement which will now be described. The linear actuator 360 contains longitudinally disposed inside and outside expandable membranes 362, 364, a front plate 366, and a rear plate 368. The front plate 366 is cylindrical in shape and includes a relatively flat base plate 370 with an inside annular flange 372 and an outside annular flange 373. The inside annular flange 372 is tube-like and contains a bore 376 that is coaxial with the longitudinal axis 342 of the brake cylinder 340 to provide a passage for the guide wire 314 to traverse. The inside annular flange 372 extends proximally from the base plate 370 to provide an inner shoulder on which the inside bellows 362 is secured.

The outside annular flange 373 is similar to the inside annular flange 372 in that it extends in the same directions as the inside annular flange 372 and provides an outer shoulder to which the outside expandable membrane 364 is secured. Attached to the distal side of the front plate 366 from inside annular flange 372 is a hypotube section 356. The hypotube section 356 is coupled to the front plate 366 and has a lumen 358 that is coaxial with the longitudinal axis 342 of the brake cylinder 340. A gas inlet 374 is disposed through the front plate 366 at a position radially outward from the longitudinal axis 342. The gas inlet 374 is in communication with a gas inlet 352 of the brake cylinder 340 via a fluid connector such as a pipe or tube 376 so that a chamber 338 receives a gas to expand the bellows created by the expandable membrane 362, 364.

Still referring to FIG. 6A, the rear plate 368 is cylindrical in shape and contains a relatively flat base plate 378, a proximally extending collet engaging ring 380, and a distal extending outside flange 382. The collet engaging ring 380 includes a bore 384 that is coaxial with the longitudinal axis 342 of the brake cylinder 340 to provide a passage for the guide wire 314 to traverse. The distal surface of the base plate also includes an inner ring 383 having the same diameter as the annular flange 372 to provide an inner shoulder to which the flexible membrane 362 is secured. The collet engaging ring 380 has an inner surface 386 that tapers to form a conical engagement surface 387 that mates with the tapered jaws of the brake collet 388 in the manner described above.

As shown in FIGS. 6A–6B, the inside and outside bellows created by the membrane 362, 364 are concentrically arranged around the longitudinal axis 342 of the brake cylinder 340. The inside and outside membranes 362, 364 are bonded to the respective shoulders as best shown in FIG. 6A, to create a substantially sealed annular chamber that may be expanded by the application of compressed gas to apply the braking force against a brake collet. The membranes 362, 364 can be secured to the respective shoulders in any manner known in the art such as glued, solvent bonded, press fit, ring clamped, rotational welded, sonically sealed or the like so that they form a leak-proof chamber.

During the operation of the brake system 310, gas is supplied to the chamber 338 created between the membranes 362, 364 through gas inlets 352, 374 when the physician activates the foot pedal to rotate the ablation burr. The gas is supplied to the gas inlets using the gas lines, manifolds, etc. as described above with respect to FIG. 3. Gas entering chamber 338 exerts pressure on the front face of the base plate 378 of rear plate 368 thereby causing the rear plate 368 to linearly translate within the bore 346 of the brake cylinder 340. As the rear plate 368 moves linearly toward the brake tube bracket 330, the conical engagement surface 387 of the rear plate 368 engages the correspondingly conical engagement surface 396 of the brake collet 388 to urge the tapered jaws 392 of the brake collet 388 radially inward to engage with the guide wire 314. The inside surface of the brake cylinder bore 346 acts as a guide so that the corresponding conical engagement surfaces are aligned properly to force the tapered jaws 392 of the brake collet 388 radially inward. The brake collet 388 clamps down onto the guide wire 314 so that the guide wire 314 is prevented from rotating. When the physician releases the foot pedal, the gas is shut off from the chamber 338 allowing the biasing force of the return spring 334 to move the rear plate 368 linearly back toward the closed end of the brake cylinder 340 as the gas escapes through the gas inlet 352. This disengages the brake tube from the guide wire.

Figure 6C:
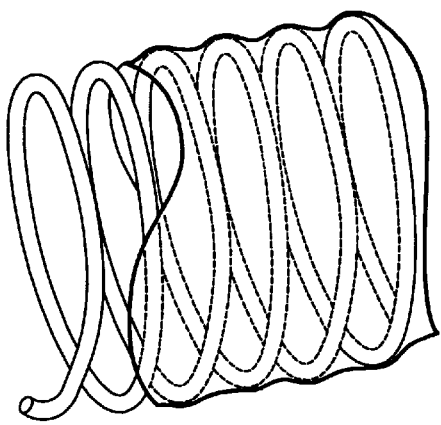

Alternatively, as will be appreciated to those skilled in the art, the linear actuator 360 of the presently preferred embodiment may use inside and outside membranes 362, 364 of a suitable material such as metal to provide a biasing force to return the rear plate 368 to its original or unexpanded position during the deactivation of the brake. Further, as shown in FIG. 6C, the inside and outside membranes could be plastic molded onto a spring. If the membranes are made so as to provide the biasing force, the return spring 334 therefore is not needed.

Figure 7:
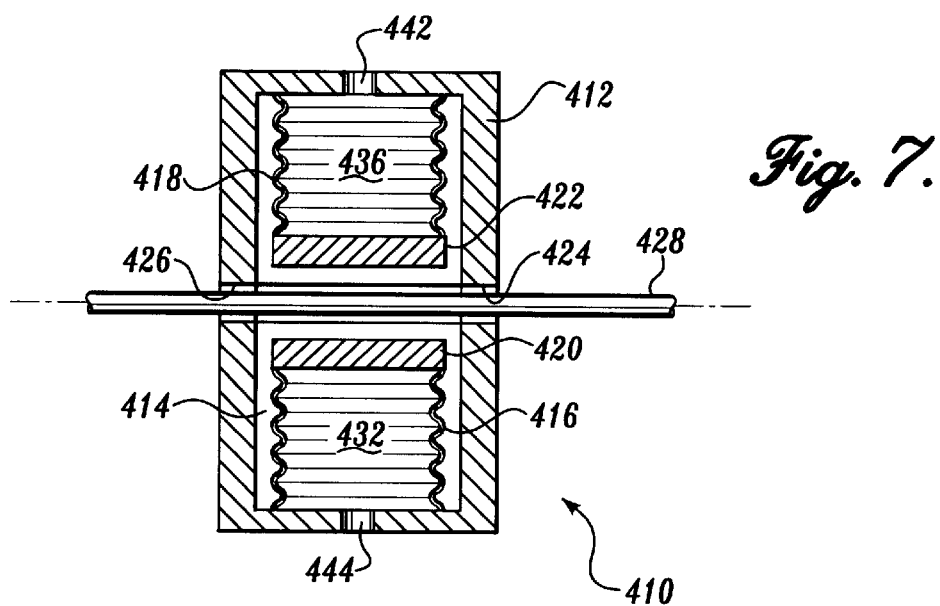
FIG. 7 illustrates a fourth embodiment of the brake activator system of the present invention.

FIG. 7 illustrates yet another embodiment of the brake system according to the present invention. The brake system 410 comprises a housing 412 having an interior cavity 414, a first and second opposing bellows 416, 418, and a pair of brake shoes 420, 422 on the opposing surfaces of the bellows 416, 418 respectively. The housing 412 has a rectangular cross-section and an aperture 424, 426 on each vertically opposing wall. The apertures 424, 426 are coaxially aligned and have a sufficient diameter to receive the guide wire 428 therethrough. Disposed within the cavity 414 are the first and second cylindrically shaped bellows 416, 418 that are positioned on opposing sides of the guide wire 428. The bottom end of the first bellows 416 is bonded to the inside face of the bottom end of the housing 412. The top end of the first bellows is bonded to the first brake shoe 420 to form a chamber 432. The top end of the second bellows 418 is bonded to the inside face of the top end of the housing 412. The bottom end of the second bellows 418 is bonded to the second brake shoe 422 to form a chamber 436. Each of the chambers 432, 436 has a gas inlet 444, 442 respectively that delivers gas to the chambers to expand the opposing bellows. The opposing brake shoes 420, 422 engage the guide wire 428 during activation of the brake system 410. The brake shoes 420, 422 may have to be constrained by housing 412 to prevent twisting or cocking of the brake shoes by the guide wire's rotational force.

During operating of the brake system 410, gas is supplied to the chambers 432, 436 of the bellows 416, 418 when the physician activates the foot pedal to rotate the ablation burr. Gas entering chambers 432, 436 exerts pressure on the brake shoes 420, 422 thereby causing the brake shoes 420, 422 to move radially inward within the cavity 414 of the housing 412 toward the guide wire 428. As the brake shoes move radially inward, the brake shoes 420, 422 engage the guide wire 428 to prevent the guide wire 428 from rotating. When the physician releases the foot pedal, the gas is shut off to the chambers 432, 436, allowing the slight biasing force of the bellows 416, 418 to disengage the brake shoes 420, 422 from the guide wire 428 as the gas escapes through the gas inlets 442, 444.

Figure 8:
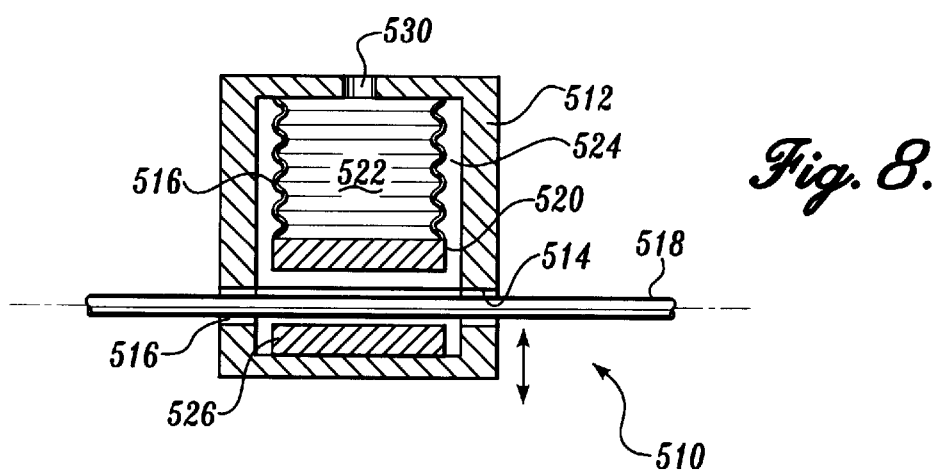
FIG. 8 illustrates a fifth embodiment of the brake activator system of the present invention.

Alternatively, FIG. 8 illustrates yet another embodiment of the brake system according to the present invention. The brake system 510 comprises a housing 512 having an interior cavity 524, a bellows 516, and a pair of brake shoes 520, 526. The housing 512 has a rectangular cross-section and a pair of aligned apertures 514, 516 on opposing walls. The apertures 514, 516 have a sufficient diameter to receive the guide wire 518. Disposed within the cavity 524 is a cylindrically shaped bellows 516 which is bonded to the top surface of the housing 512. Bonded to the bottom end of bellows 516 is a brake shoe 520 to form a chamber 522. The brake shoe 520 engages the guide wire 518 during activation of the brake system 510. Attached to the bottom surface of the housing 512 is a second brake shoe 526 having a surface for engaging the guide wire during activation of the brake system 510. A gas inlet 530 is disposed through the top end of the housing 512 in communication with chamber 522. The gas inlet 528 is in communication with a source of gas to provide the actuating force to expand the bellows 516.

During operation of the brake system 510, gas is supplied to the chamber 522 of the bellows 516 when the physician activates the foot pedal to rotate the ablation burr. Gas entering chamber 522 exerts pressure on the inside surface of brake shoe 520 thereby causing the brake shoe 520 to engage the guide wire 518. When the physician releases the foot pedal, the gas is shut off to the chamber 522, allowing the slight biasing force of the bellows 516 to disengage the brake shoe 520 from the guide wire 518 as the gas escapes through the gas inlet 530. The brake shoe 526 releases from the guide wire 518 by slack in the housing 512, allowing brake shoe 526 to drop downward slightly away from the guide wire 518.

In the presently preferred embodiments illustrated in FIGS. 7 and 8, it will be appreciated by those skilled in the art that the bellows sections could have several arrangements. For example, the bellows section in FIG. 8 could be bonded to the bottom inside surface of the housing and the second shoe could be bonded to the top inside surface of the housing. Further, it will be appreciated by those skilled in the art that the housing 412 and 512 shown in FIGS. 7 and 8, respectively, could have a C-shaped cross-section by using a part such as a C-clamp or caliper.

With respect to the above discussed embodiments and any other potential embodiments, the expandable membranes that comprise the bellows could be made of an elastomer such as latex rubber or urethane, a flexible material such as polyethylene, or a more rigid plastic such as polyester or nylon. A thin metal may also be used to form the bellows. Further, the expandable membranes could be plastic or rubber coated fabric. As described in one embodiment above, the bellows made from a metal material can have a pre-set compression biasing force so that a return spring is not needed to disengage the brake tube from the guide wire. A spring with plastic or rubber covering bonded thereto could also be used as an alternative to a metal bellows. See FIG. 6C. Bellows formed from a metal material could also be used in the embodiments described in FIGS. 7 and 8 to provide a mechanism for disengaging the brake shoe(s) from the guide wire when the ablation burr is deactivated.

While the preferred embodiment of the invention has been illustrated and described, it will be appreciated that various changes can be made therein without departing from the scope of the invention. It is therefore intended that the scope of the invention be determined from the following claims and equivalent thereto.

The embodiments of the invention in which an exclusive property or privilege is claimed are defined as follows:

1. A brake activator for use in a rotational ablation system, comprising:
    a housing including two coaxially disposed apertures for receiving a guide wire therethrough;
    a linear actuator having at least one expandable bellows; and
    a brake collet having a camming surface and a braking surface, said braking surface of said brake collet engageable with said guide wire;
    wherein the bellows are in fluid communication with a source of compressed gas that rotates an ablation burr, such that upon delivery of the compressed gas to rotate the burr the bellows expand and move a portion of the linear actuator to engagement with the brake collet and urge said braking surface of said brake collet toward said guide wire to prevent the rotation thereof.

2. The brake activator of claim 1, wherein said linear actuator includes a plurality of bellows positioned around the guide wire, each of which is in fluid communication with the compressed gas.

3. The brake activator of claim 1, wherein said linear actuator further comprises a front plate and a rear plate, said at least one expandable bellows is disposed between and coupled to said front plate and said rear plate.

4. The brake activator of claim 3, wherein said rear plate includes a collet engaging ring into which the camming surface of said brake collet is received during activation of the linear actuator to cause said braking surface of said brake collet to be engageable with said guide wire thereby preventing the rotation thereof.

5. The brake activator of claim 1, further comprising a biasing mechanism, wherein said one or more bellows has an unexpanded state and an expanded state, said biasing mechanism returns said one or more bellows to said unexpanded state.

6. A brake activator for use in a rotational ablation burr system, comprising:
    a housing;
    a linear actuator including at least one expandable bellows having an unexpanded state and an expanded state;
    a brake collet having a camming surface and a braking surface; and
    a guide wire disposed through said housing;
    wherein the bellows are activated into said expanded state in order to cause said braking surface of said brake collet to engage said guide wire thereby preventing the rotation thereof.

7. The brake activator of claim 6, wherein the bellows include a part in fluid communication with a source of driving gas that rotates the ablation burr, such that upon delivery of the driving gas to the burr, the bellows is in the expanded state and upon the cessation of driving gas to the burr, the part vents the driving gas from the bellows to enter the unexpanded state.

8. The brake activator of claim 7, wherein said linear actuator further comprising a front plate and a rear plate, said at least one expandable bellows disposed between and coupled to said front plate and said rear plate.

9. The brake activator of claim 8, wherein said rear plate includes a collet engaging surface, said collet engagement surface of said rear plate engages said camming surface of said brake collet during activation of the linear actuator to cause said braking surface of said brake collet to engage said guide wire thereby preventing the rotation thereof.

10. The brake activator of claim 8, wherein said at least one bellows includes a plurality of bellows, said ends of each of the plurality of bellows are coupled to said front plate and said rear plate in a radial configuration.

11. The brake activator of claim 7, further comprising a biasing mechanism, wherein said biasing mechanism returns said bellows to said unexpanded state.

12. A brake activator for use in a rotational ablation burr system, comprising:
- a housing including two coaxially aligned apertures for receiving a guide wire therethrough;
- at least one expandable bellows; and
- a pair of brake shoes, each brake shoe having a braking surface, at least one of said pair of brake shoes coupled to at least one bellows;
- wherein expansion of said at least one bellows moves the braking surface coupled thereto to engage said guide wire, said guide wire compressed between said pair of brake shoes.

13. The brake activator of claim 12, further comprising two bellows, wherein each of said pair of brake shoes is coupled to one of each of said two bellows.

14. The brake activator of claim 13, wherein said two bellows expands radially inward toward said guide wire.

15. The brake activator of claim 12, wherein one of said pair of brake shoes is coupled to said housing.

16. A guide wire brake activation system comprising:
- a housing;
- a linear actuator disposed within the housing; the linear actuator comprising:
  - at least one bellows;
  - a front plate; and
  - a rear plate, the expandable bellows attached between said front plate and said rear plate to form an expandable chamber;
- a brake collet having a camming surface and a braking surface; and
- a guide wire disposed through the housing;
- wherein expansion of the chamber causes said rear plate to move and engage said camming portion of said brake collet to urge said braking surface into a clamping engagement with said guide wire to prevent the rotation thereof.

* * * * *

UNITED STATES PATENT AND TRADEMARK OFFICE
CERTIFICATE OF CORRECTION

PATENT NO.     : 6,626,923 B1
DATED          : September 30, 2003
INVENTOR(S)    : M.H. Wyzgala It is certified that error appears in the above-identified patent and that said Letters Patent is hereby corrected as shown below:

<u>Title page,</u>
Item [56], References Cited, U.S. PATENT DOCUMENTS, insert:
-- 4,679,557   7/1987      Opie et al.
4,926,858      5/1990      Gifford III et al.
5,011,490      4/1991      Fischell et al.
5,314,407      5/1994      Auth et al.
5,490,859      2/1996      Mische et al.
5,501,694      3/1996      Ressemann et al.
5,584,843      12/1996     Wulfman et al.
5,667,490      9/1997      Keith et al.
5,779,722      7/1998      Shturman et al.
5,893,857      4/1999      Shturman et al. --

Item [57], ABSTRACT,
Line 2, "that when actuated," should read -- that, when actuated, --
Line 3, "prevent" should read -- prevents --

<u>Column 10,</u>
Lines 42 and 59, "wire thereby" should read -- wire, thereby --

<u>Column 11,</u>
Line 2, "comprising" should read -- comprises --
Line 9, "wire thereby" should read -- wire, thereby --

Signed and Sealed this

Thirteenth Day of April, 2004

JON W. DUDAS
*Acting Director of the United States Patent and Trademark Office*